(12) United States Patent
Husom

(10) Patent No.: US 7,191,552 B1
(45) Date of Patent: Mar. 20, 2007

(54) FOOT ROLLOVER PREVENTIVE FOOTWEAR SOLE

(76) Inventor: Danny Bruce Husom, 804 Circle Dr., Buffalo, MN (US) 55313

( * ) Notice: Subject to any disclaimer, the term of this patent is extended or adjusted under 35 U.S.C. 154(b) by 136 days.

(21) Appl. No.: 11/073,439

(22) Filed: Mar. 8, 2005

(51) Int. Cl.
A61F 5/14 (2006.01)

(52) U.S. Cl. .......................... 36/144; 36/30 R

(58) Field of Classification Search .......... 36/142–144, 36/127
See application file for complete search history.

(56) References Cited

U.S. PATENT DOCUMENTS

| 4,642,911 A | * | 2/1987 | Talarico, II | 36/30 R |
| 4,882,856 A | * | 11/1989 | Glancy | 36/43 |
| 6,725,578 B2 | * | 4/2004 | Kerrigan | 36/144 |

* cited by examiner

Primary Examiner—Ted Kavanaugh

(57) ABSTRACT

A footwear sole for providing firmness and support to the lateral edge of a person's foot. The footwear sole includes a plurality of layers of material including a first layer of material having a definite thickness and also including a second layer of material also having a definite thickness with the second layer of material being softer than the first layer of material.

8 Claims, 2 Drawing Sheets

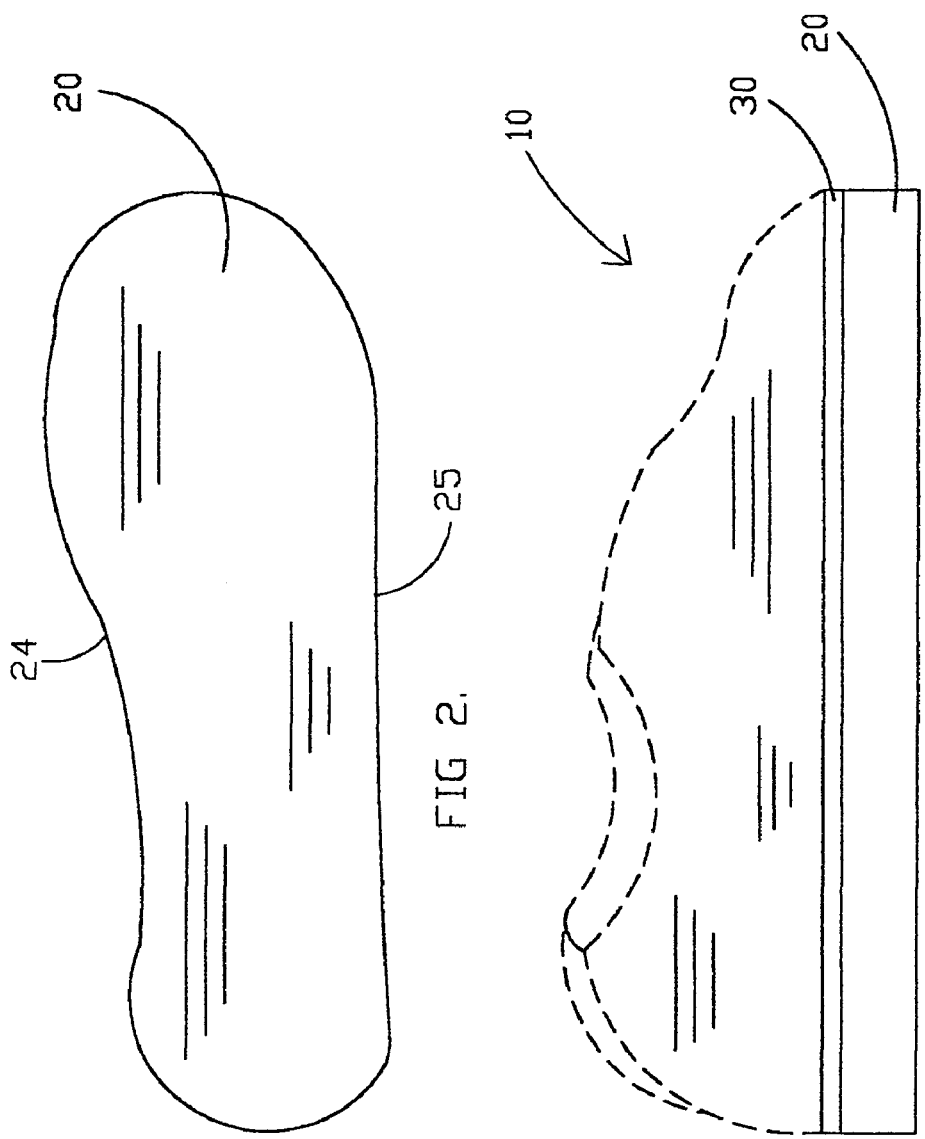
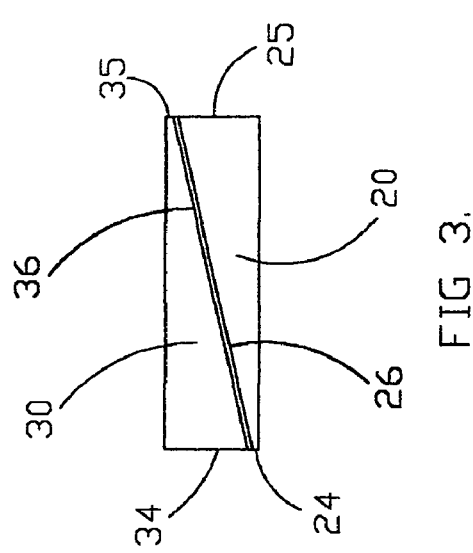

FOOT ROLLOVER PREVENTIVE FOOTWEAR SOLE

BACKGROUND OF THE INVENTION

1. Field of the Invention

The present invention relates to soles for footwear and more particularly pertains to a new footwear sole that negates the inherent negative qualities of compressive EVA and urethane and provides for a more normal biomechanical function.

2. Description of the Prior Art

The use of soles for footwear is known in the prior art. More specifically, soles for footwear heretofore devised and utilized are known to consist basically of familiar, expected and obvious structural configurations, notwithstanding the myriad of designs encompassed by the crowded prior art that have been developed for the fulfillment of countless objectives and requirements.

The prior art includes footwear soles having layers with equal densities throughout which causes pathological foot problems such as acquired flat foot and atrophy of medial foot anatomy, i.e. medial band of the plantar fascia.

SUMMARY OF THE INVENTION

The general purpose of the present invention, which will be described subsequently in greater detail, is to provide a new footwear sole which has many of the advantages of the soles for footwear mentioned heretofore and many novel features that result in a new footwear sole which is not anticipated, rendered obvious, suggested, or even implied by any of the prior art soles for footwear, either alone or in any combination thereof. The present invention includes a plurality of layers of material including a first layer of material having a definite thickness and also including a second layer of material also having a definite thickness with the second layer of material being softer than the first layer of material. None of the prior art includes the combination of the elements in gradient form of the present invention.

There has thus been outlined, rather broadly, the more important features of the footwear sole in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

It is an object of the present invention to provide a new footwear sole which has many of the advantages of the soles for footwear mentioned heretofore and many novel features that result in a new footwear sole which is not anticipated, rendered obvious, suggested, or even implied by any of the prior art soles for footwear, either along or in any combination thereof.

Still another object of the present invention is to provide a new footwear sole for providing firmness and support to the lateral edge of a person's foot.

Still yet another object of the present invention is to provide a new footwear sole that controls the movement of mass away from the centerline as the user walks.

Even still another object of the present invention is to provide anew footwear sole that prevents foot problems such as Plantar Fascilitis and flat feet by providing more firmness under the lateral side of the foot that bends outwardly upon the user walking.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 1 is a right side elevational view of a new footwear sole according to the present invention.

FIG. 2 is a bottom planar view of the present invention.

FIG. 3 is a rear elevational view of the present invention.

DESCRIPTION OF THE PREFERRED EMBODIMENT

Figure 4:
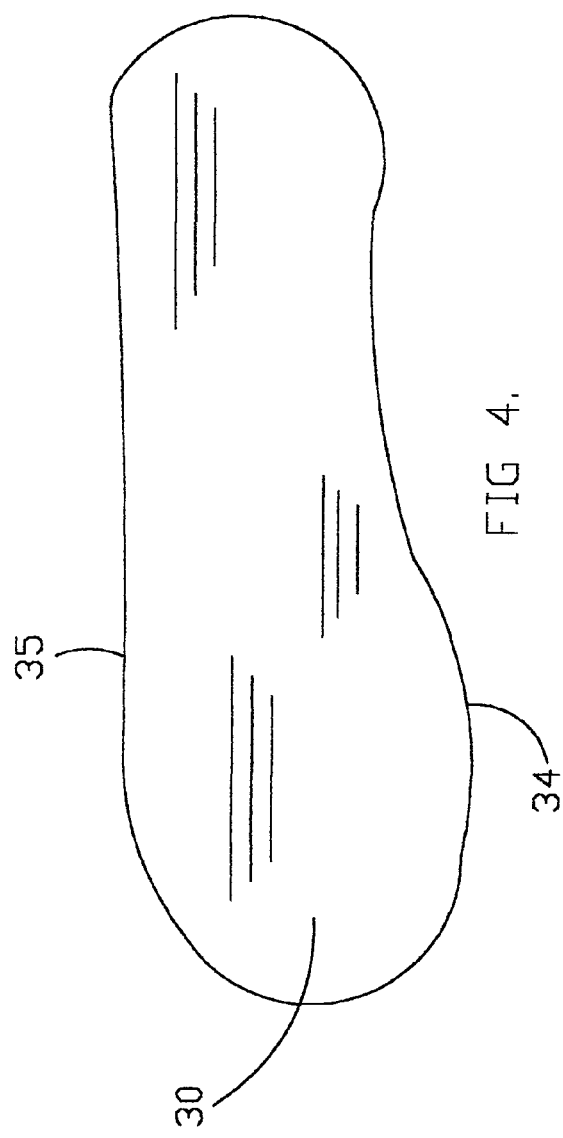
FIG. 4 is a top planar view of the present invention.
Figure 5:
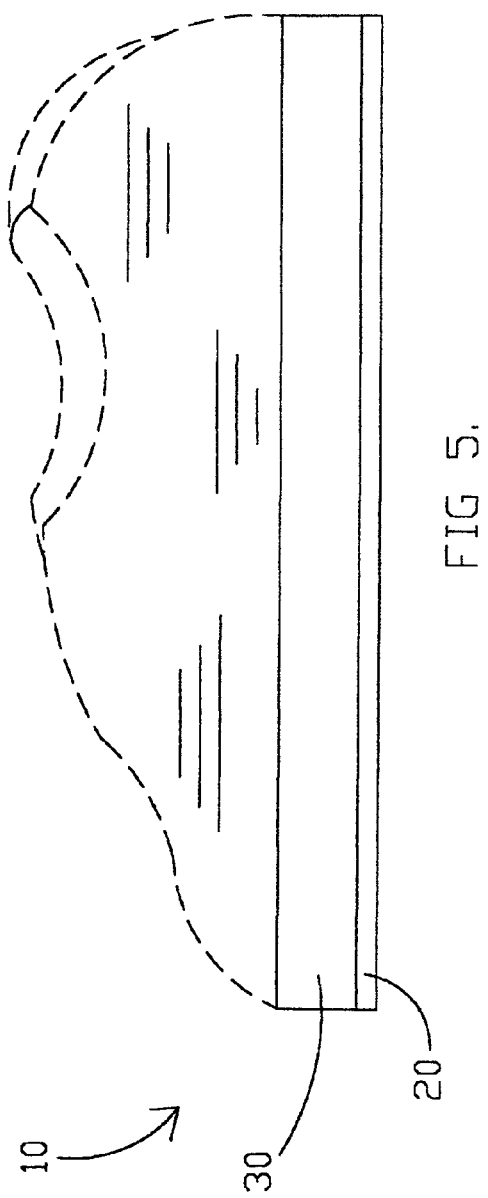
FIG. 5 is a left side elevational view of the present invention.

With reference now to the drawings, and in particular to FIGS. 1 through 5 thereof, a new footwear sole embodying the principles and concepts of the present invention and generally designated by the reference numeral 10 will be described.

As best illustrated in FIGS. 1 through 5, the footwear sole 10 generally comprises a plurality of layers of material including a first layer of material 20 having a definite thickness and also including a second layer of material 30 also having a definite thickness. The second layer of material 30 is softer than the first layer of material 20. The second layer of material 30 is conventionally supported and disposed upon the first layer of material 20. Each of the first and second layers of material 20, 30 has a longitudinal medial edge 24, 34 and a longitudinal lateral edge 25, 35. The longitudinal medial edge 24, 34 is adapted to support a portion of a person's instep. The longitudinal medial edge 24, 34 extends an entire length of the footwear sole 10 and supports and extends from a user's big toe to a user's heel. The longitudinal lateral edge 25, 35 extends the entire length of the footwear sole 10 and supports and extends from a user's little toe to the user's heel.

Each of the first and second layers of material 30, 30 is wedge-shaped. The first layer of material 20 is tapered from the entire length of the longitudinal lateral edge 25 to the entire length of the longitudinal medial edge 24 of the first layer of material 20. The second layer of material 30 is tapered from the entire length of the longitudinal medial edge 34 to the entire length of the longitudinal lateral edge 35 of the second layer of material 30. The second layer of material 30 has a durometer hardness ranging from 40% to 60% of the durometer hardness of the first layer of material 20. The second layer of material 30 has a durometer hardness of approximately ½ of that of the first layer of material 20. The second layer of material 30 has a bottom surface 36 which is angled from 10 degrees to 40 degrees relative to the longitudinal medial edge 34 of the second layer of material 30. The first layer of material 20 has a top surface 26 which is angled from 10 degrees to 40 degrees relative to the longitudinal lateral edge 25 of the first layer of material 20. The longitudinal lateral edge 25 of the first layer of material 20 is thicker than the longitudinal lateral edge 35 of the second layer of material 30 to provide more firmness and support along the lateral edge of the user's foot than along the medial edge of the user's foot where the longitudinal medial edge 34 of the second layer of material 30 is thicker than the longitudinal medial edge 25 of the first layer of material 20 and to prevent the user from rolling over on the longitudinal lateral edge of the user's foot as the user walks.

The direction of a user's foot at heel strick as the user walks is away from the centerline of the user's body. The biomechanics of the user's foot along with the user's knee and hip rotation causes the motion and mass of the user's body to move toward the centerline of the user's body and the sole of the footwear compresses downwardly and bends outwardly along the longitudinal lateral edge 25, 35 thus causing foot problems including Plantar Fasciitis and flat feet. The footwear sole 10 of the present invention prevents these foot problems by creating more firmness along the outer or lateral part of the foot which includes the longitudinal lateral edges 25, 35 of the first and second layers of material 20, 30; whereas, the prior art exasperates the foot problems by creating a footwear sole which has an even density throughout the layers of material; whereas, the footwear sole 10 of the present invention has wedge-shaped layers of material 20, 30 with the firmer material having a greater density along the longitudinal lateral edge 25 of the first layer of material 20 of the footwear sole 10 upon which the foot bends outwardly as the user walks.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the footwear sole. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A footwear sole comprising:
a plurality of layers of material including a first layer of material having a definite thickness and also including a second layer of material also having a definite thickness, said second layer of material being softer than said first layer of material, said second layer of material being disposed upon said first layer of material, each of said first and second layers of material having a longitudinal medial edge and a longitudinal lateral edge, said longitudinal medial edge including a portion of an instep, said longitudinal medial edge extending an entire length of said footwear sole and supporting and extending from a user's big toe to a user's heel, said longitudinal lateral edge extending an entire length of said footwear sole and supporting and extending from a user's little toe to the user's heel, said first layer of material being tapered from the entire length of said longitudinal lateral edge to the entire length of said longitudinal medial edge of said first layer of material to provide firmness and support along a lateral edge of the user's foot which extends from the user's heel to the user's little toe, and to prevent the user from rolling over on the longitudinal lateral edge of the user's foot as the user walks.

2. The footwear sole as described in claim 1, wherein said second layer of material is tapered from the entire length of said longitudinal medial edge to the entire length of said longitudinal lateral edge of said second layer of material.

3. The footwear sole as described in claim 2, wherein each of said first and second layers of material is wedge-shaped.

4. The footwear sole as described in claim 2, wherein said second layer of material has a bottom surface which is angled from 10 degrees to 40 degrees relative to said longitudinal medial edge of said second layer of material.

5. The footwear sole as described in claim 4, wherein said first layer of material has a top surface which is angled from 10 degrees to 40 degrees relative to said longitudinal lateral edge of said first layer of material.

6. The footwear sole as described in claim 2, wherein said second layer of material has a durometer hardness ranging from 40% to 60% of the durometer hardness of said first layer of material to substantially prevent the footwear sole from compressing downwardly and bending outwardly along the longitudinal lateral edge.

7. The footwear sole as described in claim 6, wherein said second layer of material has a durometer hardness of approximately ½ of that of said first layer of material.

8. The footwear sole as described in claim 7, wherein said longitudinal lateral edge of said first layer of material is thicker than said longitudinal lateral edge of said second layer of material to provide more firmness and support along the lateral edge of the user's foot than along the medial edge of the user's foot where said longitudinal medial edge of said second layer of material is thicker than said longitudinal medial edge of said first layer of material.

* * * * *